US006488926B1

(12) United States Patent
Khan et al.

(10) Patent No.: US 6,488,926 B1
(45) Date of Patent: *Dec. 3, 2002

(54) VACCINE COMPOSITIONS

(75) Inventors: Mohammed Anjam Khan, Newcastle upon Tyne (GB); Carlos Estenio Hormaeche, Newcastle upon Tyne (GB); Steven Neville Chatfield, London (GB); Gordon Dougan, London (GB)

(73) Assignee: Medeva Holdings B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/586,740

(22) PCT Filed: Jul. 29, 1994

(86) PCT No.: PCT/GB94/01647

§ 371 (c)(1),
(2), (4) Date: Jul. 19, 1996

(87) PCT Pub. No.: WO95/04151

PCT Pub. Date: Feb. 9, 1995

(30) Foreign Application Priority Data

Jul. 30, 1993  (WO) .............................. PCT/GB93/01617
Jan. 31, 1994  (GB) ................................................ 9401787

(51) Int. Cl.[7] ..................... A01N 63/00; A61K 39/00; C12N 15/00; C07H 21/04
(52) U.S. Cl. ................ 424/93.1; 424/184.1; 424/193.1; 424/197.11; 435/252.3; 435/320.1; 435/325; 530/350; 530/402; 536/23.4
(58) Field of Search ..................... 536/23.4; 435/320.1, 435/325, 252.3; 530/350, 402; 424/93.1, 184.1, 193.1, 197.11

(56) References Cited

U.S. PATENT DOCUMENTS 5,443,966 A * 8/1995 Fairweather et al.
5,498,538 A * 3/1996 Kay et al.

FOREIGN PATENT DOCUMENTS

| EP | 209281 | * | 1/1987 |
| EP | A 0 432 965 | | 6/1991 |
| WO | WO/A 89/06974 | | 8/1989 |
| WO | WO/A 91 09621 | | 7/1991 |
| WO | WO/A 92 15689 | | 9/1992 |
| WO | 92/16557 | * | 10/1992 |
| WO | WO/A 93 08290 | | 4/1993 |
| WO | WO/A 94 03615 | | 2/1994 |

OTHER PUBLICATIONS

Chatfield et al., Dev. Biol. Stand. 82: 35–42 (1994).
Fairweather et al., J. of Bacteriol. 165(1): 21–27 (1986).
"Use Of The nirB Promoter To Direct The Stable Expression Of Heterologous Antigens In Salmonella Oral Vaccine Strains: Development of A Single–Dose Oral Tetanus Vaccine", by S.N. Chatfield et al., Bio/Technology, vol. 10, Aug. 1992, pp. 888–892.
"Analysis Of T and B Cell Epitopes Of The *Schistosoma mansoni* P28 Antigen In The Rat Model By Using Synthetic Peptides", by Claude Auriault, et al., The Journal of Immunology, vol. 141, No. 5, Sep. 1, 1988, pp. 1687–1694.
"High level heterologous expression in *E. coli* using the anaerobically–activated nirB pomoter", by M.D. Oxer. et al., Nucleic Acids Research, vol. 19, No. 11, Jun. 11, 1991, pp. 2889–2892.
Freer, J. et al. (Ed.) 6th European Workshop, Stirling, Scotland, UK, Jun. 27–Jul. 2, 1993: the whole document: FEMS Symposium, No. 73, Bacterial Protein Toxins: Gustav Fisher Verlag; Stuttgart German; O (O) 1994.

* cited by examiner

*Primary Examiner*—Mark Navarro
(74) *Attorney, Agent, or Firm*—Wolf, Greenfield & Sacks, P.C.

(57) ABSTRACT

The invention provides a DNA construct comprising a DNA sequence encoding a fusion protein of the formula: TetC-$(Z)_a$-Het, wherein: TetC is the C fragment of tetanus toxin, or a protein comprising the epitopes thereof; Het is a heterologous protein, Z is an amino acid, and a is zero or a positive integer, provided that $(Z)_a$ does not include the sequence Gly-Pro. The invention also provides replicable expression vectors containing the constructs, bacteria transformed with the constructs, the fusion proteins per se and vaccine compositions formed from the fusion proteins or attenuated bacteria expressing the fusion proteins.

22 Claims, 5 Drawing Sheets

VACCINE COMPOSITIONS

This invention relates to DNA constructs, replicable expression vectors containing the constructs, bacteria containing the constructs and vaccines containing the bacteria or fusion proteins expressed therefrom. More particularly, the invention relates to novel DNA constructs encoding the C-fragment of tetanus toxin, and to fusion proteins containing tetanus toxin C-fragment.

It is known to prepare DNA constructs encoding two or more heterologous proteins with a view to expressing the proteins in a suitable host as a single fusion protein. However, it has often been found that fusing two proteins together in this way leads to an incorrectly folded chimaeric protein which no longer retains the properties of the individual components. For example, the B-subunits of the *Vibrio cholerae* (CT-B) and *E. coli* (LT-B) enterotoxins are powerful mucosal immunogens but genetic fusions to these subunits can alter the structure and properties of the carriers and hence their immunogenicity (see M. Sandkvist et al. J. Bacteriol. 169, pp4570–6, 1987, Clements et al. 1990 and M. Lipscombe et al. Mol. Microbiol. 5, pp 1385, 1990). Moreover, many heterologous proteins expressed in bacteria are not produced in soluble properly folded or active forms and tend to accumulate as insoluble aggregates (see C. Schein et al. Bio/Technology 6, pp 291–4, 1988 and R. Halenbeck et al. Bio/Technology 7, pp 710–5, 1989.

In our earlier unpublished international patent application PCT/GB93/01617, it is disclosed that by providing a DNA sequence encoding tetanus toxin C-fragment (TetC) linked via a "hinge region" to a second sequence encoding an antigen, the expression of the sequence in bacterial cells is enhanced relative to constructs wherein the C-fragment is absent. For example, the expression level of the full length P28 glutathione S-tranferase protein of *S. mansoni* when expressed as a fusion to TetC from the nirB promoter was greater than when the P28 protein was expressed alone from the nirB promoter. The TetC fusion to the full length P28 protein of *S. mansoni* was soluble and expressed in both *E. coli* and *S. typhimurium*. In addition, the TetC-P28 fusion protein was capable of being affinity purified by a glutathione agarose matrix, suggesting that the P28 had folded correctly to adopt a conformation still capable of binding to its natural substrate. It was previously considered that a hinge region, which typically is a sequence encoding a high proportion of proline and/or glycine amino acids, is essential for promoting the independent folding of both the TetC and the antigenic protein fused thereto. However, it has now been discovered, surprisingly in view of the previous studies on CT-B and LT-B referred to above, that when the hinge region is omitted between the TetC and a second antigen such as P28, the proteins making up the fusion do exhibit correct folding as evidenced by affinity purification on a glutathione agarose matrix.

Accordingly, in a first aspect, the invention provides a DNA construct comprising a DNA sequence encoding a fusion protein of the formula TetC-$(Z)_a$-Het, wherein TetC is the C fragment of tetanus toxin, or a protein comprising the epitopes thereof; Het is a heterologous protein; Z is an amino acid, and a is zero or a positive integer, provided that $(Z)_a$ does not include the sequence Gly-Pro.

Typically $(Z)_a$ is a chain of 0 to 15 amino acids, for example 0 to 10, preferably less than 6 and more preferably less than 4 amino acids.

In one embodiment $(Z)_a$ is a chain of two or three amino acids, the DNA sequence for which defines a restriction endonuclease cleavage site.

In another embodiment, a is zero.

Usually the group $(Z)_a$ will not contain, simultaneously, both glycine and proline, and generally will not contain either glycine or proline at all.

In a further embodiment, $(Z)_a$ is a chain of amino acids provided that when a is 6 or more, $(Z)_a$ does not contain glycine or proline.

The group $(Z)_a$ may be a chain of amino acids substantially devoid of biological activity.

In a second aspect the invention provides a replicable expression vector, for example suitable for use in bacteria, containing a DNA construct as hereinbefore defined.

In another aspect, the invention provides a host (e.g. a bacterium) containing a DNA construct as hereinbefore defined, the DNA construct being present in the host either in the form of a replicable expression vector such as a plasmid, or being present as part of the host chromosome, or both.

In a further aspect, the invention provides a fusion protein of the form TetC-$(Z)_a$-Het as hereinbefore defined, preferably in substantially pure form, said fusion protein being expressible by a replicable expression vector as hereinbefore defined.

In a further aspect the invention provides a process for the preparation of a bacterium (preferably an attenuated bacterium) which process comprises transforming a bacterium (e.g. an attenuated bacterium) with a DNA construct as hereinbefore defined.

The invention also provides a vaccine composition comprising an attenuated bacterium, or a fusion protein, as hereinbefore defined, and a pharmaceutically acceptable carrier.

The heterologous protein "Het" may for example be a heterologous antigenic sequence, e.g. an antigenic sequence derived from a virus, bacterium, fungus, yeast or parasite.

Examples of viral antigenic sequences are sequences derived from a type of human immunodeficiency virus (HIV) such as HIV-1 or HIV-2, the CD4 receptor binding site from HIV, for example from HIV-1 or -2., hepatitis A, B or C virus, human rhinovirus such as type 2 or type 14, Herpes simplex virus, poliovirus type 2 or 3, foot-and-mouth disease virus (FMDV), rabies virus, rotavirus, influenza virus, coxsackie virus, human papilloma virus (HPV), for example the type 16 papilloma virus, the E7 protein thereof, and fragments containing the E7 protein or its epitopes; and simian immunodeficiency virus (SIV).

Examples of antigens derived from bacteria are those derived from *Bordetella pertussis* (e.g. P69 protein and filamentous haemagglutinin (FHA) antigens), *Vibrio cholerae*, *Bacillus anthracis*, and *E.coli* antigens such as *E.coli* heat Labile toxin B subunit (LT-B), *E.coli* K88 antigens, and enterotoxigenic *E.coli* antigens. Other examples of antigens include the cell surface antigen CD4, *Schistosoma mansoni* P28 glutathione S-transferase antigens (P28 antigens) and antigens of flukes, mycoplasma, roundworms, tapeworms, *Chlamydia trachomatis*, and malaria parasites, eg. parasites of the genus plasmodium or babesia, for example *Plasmodium falciparum*, and peptides encoding immunogenic epitopes from the aforementioned antigens.

Particular antigens include the full length *Schistosoma mansoni* P28, and oligomers (e.g. 2, 4 and 8-mers) of the immunogenic P28 aa 115–131 peptide (which contains both a B and T cell epitope), and human papilloma virus E7 protein, Herpes simplex antigens, foot and mouth disease virus antigens and simian immunodeficiency virus antigens.

The DNA constructs of the present invention may contain a promoter whose activity is induced in response to a change in the surrounding environment. An example of such a promoter sequence is one which has activity which is induced by anaerobic conditions. A particular example of such a promoter sequence is the nirB promoter which has been described, for example in International Patent Application PCT/GB92/00387. The nirB promoter has been isolated from *E.coli*, where it directs expression of an operon which includes the nitrite reductase gene nirB (Jayaraman et al, J. Mol. Biol. 196, 781–788, 1987), and nirD, nirC, cysG (Peakman et al, Eur. J. Biochem. 191, 315323, 1990). It is regulated both by nitrite and by changes in the oxygen tension of the environment, becoming active when deprived of oxygen, (Cole, Biochem, Biophys. Acta. 162, 356–368, 1968). Response to anaerobiosis is mediated through the protein FNR, acting as a transcriptional activator, in a mechanism common to many anaerobic respiratory genes. By deletion and mutational analysis the part of the promoter which responds solely to anaerobiosis has been isolated and by comparison with other anaerobically regulated promoters a consensus FNR-binding site has been identified (Bell et al, Nucl, Acids. Res. 17, 3865–3874, 1989; Jayaraman et al, Nucl, Acids, Res. 17, 135–145, 1989). It has also been shown that the distance between the putative FNR-binding site and the −10 homology region is critical (Bell et al, Molec. Microbiol.4, 1753–1763, 1990). It is therefore preferred to use only that part of the nirB promoter which responds solely to anaerobiosis. As used herein, references to the nirB promoter refer to the promoter itself or a part or derivative thereof which is capable of promoting expression of a coding sequence under anaerobic conditions. The preferred sequence, and which contains the nirB promoter is:

AATTCAGGTAAATTTGATGTACAT-
CAAATGGTACCCCTTGCTGAATCGTTAAGG
TAGGCGGTAGGGCC (SEQ ID NO: 1)

In a most preferred aspect, the present invention provides a DNA molecule comprising the nirB promoter operably linked to a DNA sequence encoding a fusion protein as hereinbefore defined.

In another preferred aspect of the invention, there is provided a replicable expression vector, suitable for use in bacteria, containing the nirB promoter sequence operably linked to a DNA sequence encoding a fusion protein as hereinbefore defined.

The DNA molecule or construct may be integrated into the bacterial chromosome, e.g. by methods known per se, and thus in a further aspect, the invention provides a bacterium having in its chromosome, a DNA sequence or construct as hereinbefore defined.

Stable expression of the fusion protein can be obtained in vivo. The fusion protein can be expressed in an attenuated bacterium which can thus be used as a vaccine.

The attenuated bacterium may be selected from the genera Salmonella, Bordetella, Vibrio, Haemophilus, Neisseria and Yersinia. Alternatively, the attenuated bacterium may be an attenuated strain of enterotoxigenic *Escherichia coli*. In particular the following species can be mentioned: *S.typhi*—the cause of human typhoid; *S.typhimurium*—the cause of salmonellosis in several animal species; *S.enteritidis*—a cause of food poisoning in humans; *S.choleraesuis*—a cause of salmonellosis in pigs; *Bordetella pertussis*—the cause of whooping cough; *HaemoDhilus influenzae*—a cause of meningitis; *Neisseria gonorrhoea* the cause of gonorrhoea; and Yersinia—a cause of food poisoning.

Examples of attenuated bacteria are disclosed in, for example EP-A-0322237 and EP-A-0400958, the disclosures in which are incorporated by reference herein.

An attenuated bacterium containing a DNA construct according to the invention, either present in the bacterial chromosome, or in plasmid form, or both, can be used as a vaccine. Fusion proteins (preferably in substantially pure form) expressed by the bacteria can also be used in the preparation of vaccines. For example, a purified TetC-P28 fusion protein in which the TetC protein is linked via its C-terminus to the P28 protein with no intervening hinge region has been found to be immunogenic on its own. In a further aspect therefore, the invention provides a vaccine composition comprising a pharmaceutically acceptable carrier or diluent and, as active ingredient, an attenuated bacterium or fusion protein as hereinbefore defined.

The vaccine may comprise one or more suitable adjuvants.

The vaccine is advantageously presented in a lyophilised form, for example in a capsular form, for oral administration to a patient. Such capsules may be provided with an enteric coating comprising, for example, Eudragit "S", Eudragit "L", Cellulose acetate, Cellulose acetate phthalate or Hydroxypropylmethyl Cellulose. These capsules may be used as such, or alternatively, the lyophilised material may be reconstituted prior to administration, e.g. as a suspension. Reconstitution is advantageously effected in buffer at a suitable pH to ensure the viability of the organisms. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramammary administration.

The attenuated bacterium containing the DNA construct or fusion protein of the invention may be used in the prophylactic treatment of a host, particularly a human host but also possibly an animal host. An infection caused by a microorganism, especially a pathogen, may therefore be prevented by administering an effective dose of an attenuated bacterium according to the invention. The bacterium then expresses the fusion protein which is capable of raising antibody to the micro-organism. The dosage employed will be dependent on various factors including the size and weight of the host, the type of vaccine formulated and the nature of the fusion protein.

An attenuated bacterium according to the present invention may be prepared by transforming an attenuated bacterium with a DNA construct as hereinbefore defined. Any suitable transformation technique may be employed, such as electroporation. In this way, an attenuated bacterium capable of expressing a protein or proteins heterologous to the bacterium may be obtained. A culture of the attenuated bacterium may be grown under aerobic conditions. A sufficient amount of the bacterium is thus prepared for formulation as a vaccine, with minimal expression of the fusion protein occurring.

The DNA construct may be a replicable expression vector comprising the nirB promoter operably linked to a DNA sequence encoding the fusion protein. The nirB promoter may be inserted in an expression vector, which already incorporates a gene encoding one of the heterologous proteins (e.g. the tetanus toxin C fragment), in place of the existing promoter controlling expression of the protein. The gene encoding the other heterologous protein (e.g. an antigenic sequence) may then be inserted. The expression vector should, of course, be compatible with the attenuated bacterium into which the vector is to be inserted.

The expression vector is provided with appropriate transcriptional and translational control elements including, besides the nirB promoter, a transcriptional termination site and translational start and stop codons. An appropriate ribosome binding site is provided. The vector typically comprises an origin of replication and, if desired, a selectable marker gene such as an antibiotic resistance gene. The vector may be a plasmid.

The invention will now be illustrated but not limited, by reference to the following examples and the accompanying drawings, in which.

In accordance with the invention a vector was constructed to allow genetic fusions to the C-terminus of the highly immunogenic C fragment of tetanus toxin, without the use of a heterologous hinge domain. A fusion was constructed, with the gene encoding the protective 28 kDa glutathione S-transferase from *Schistosoma mansoni*. The recombinant vector was transformed into Salmonella typhimurium (SL338; rm⁺). The resulting chimeric protein was stably expressed in a soluble form in salmonella as assessed by western blotting with fragment C and glutathione S-transferase antisera. Furthermore it was found that the P28 component of the fusion retains the capacity to bind glutathione.

The construction of the vector and the properties of the fusion protein expressed therefrom are described in more detail below.

EXAMPLE 1

Preparation of pTECH1

Figure 1:
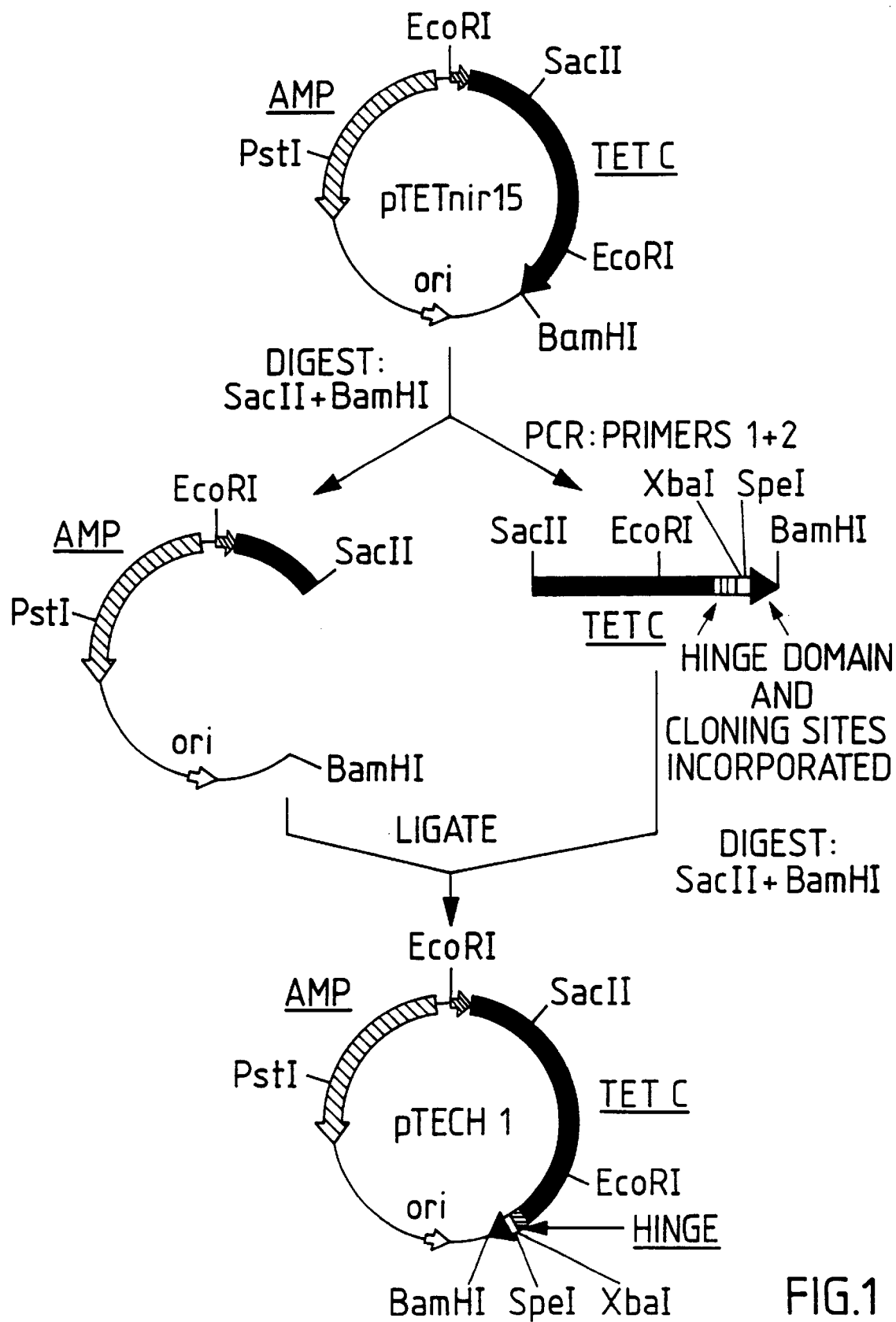
FIG. 1 is a schematic illustration of the construction of plasmid pTECH1.
Figure 2:
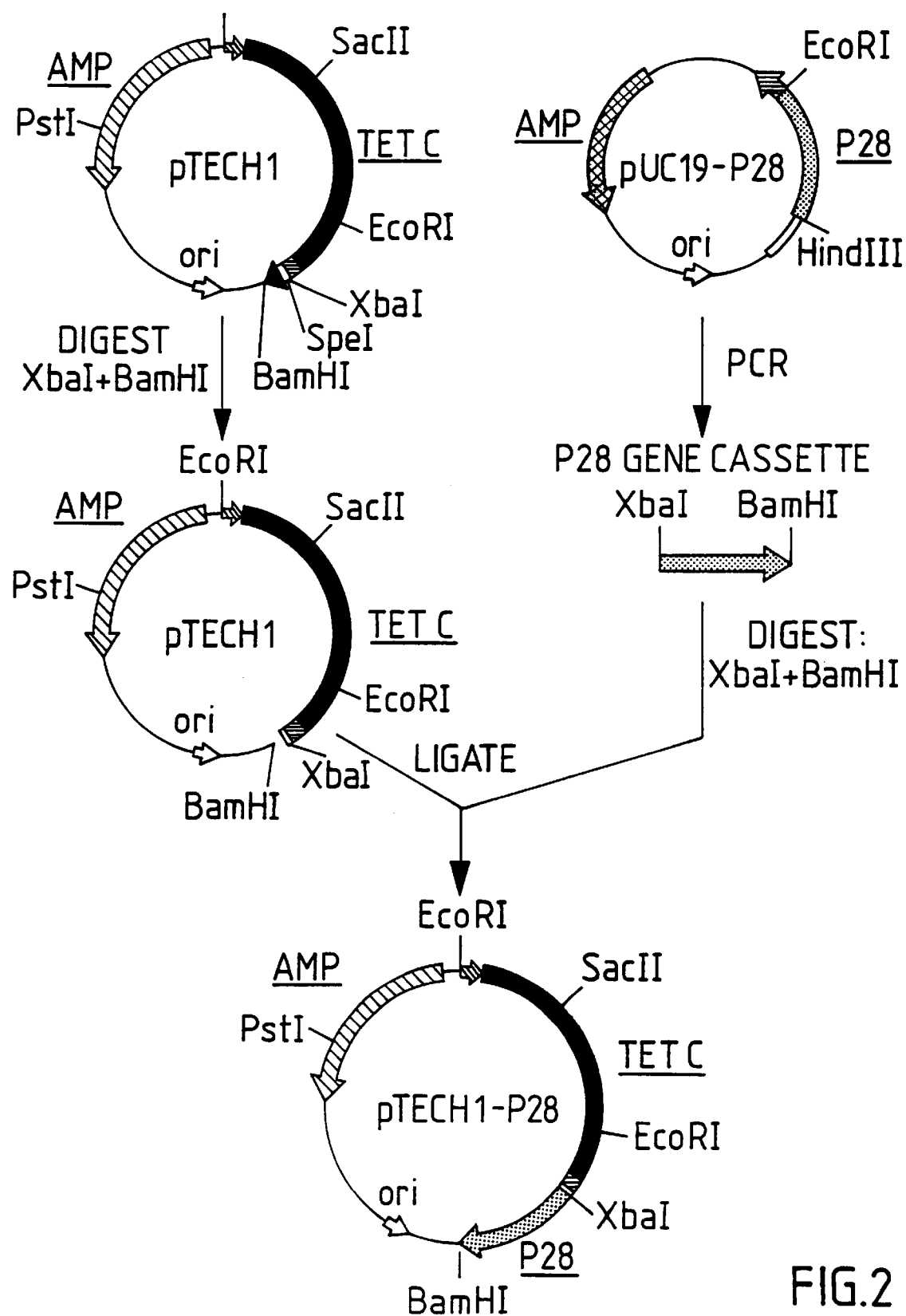
FIG. 2 illustrates schematically the preparation of the plasmid pTECH1-28 from the starting materials pTECH1 and PUC19-P28.
Figure 3:
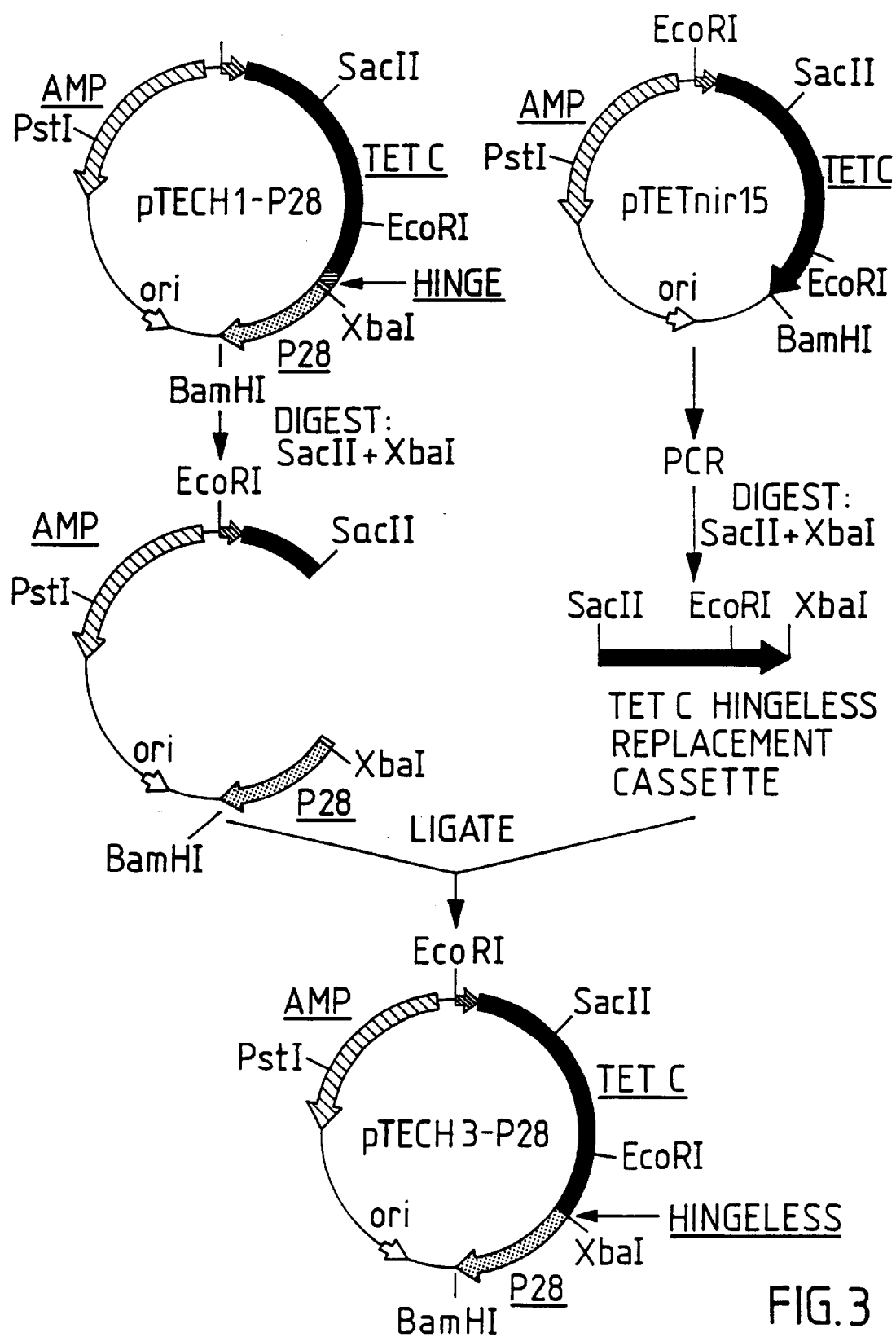
FIG. 3 illustrates schematically the preparation of the plasmid pTECH3-P28 from the starting materials plasmids pTECH1-P28 and pTETnir15.
Figure 4:
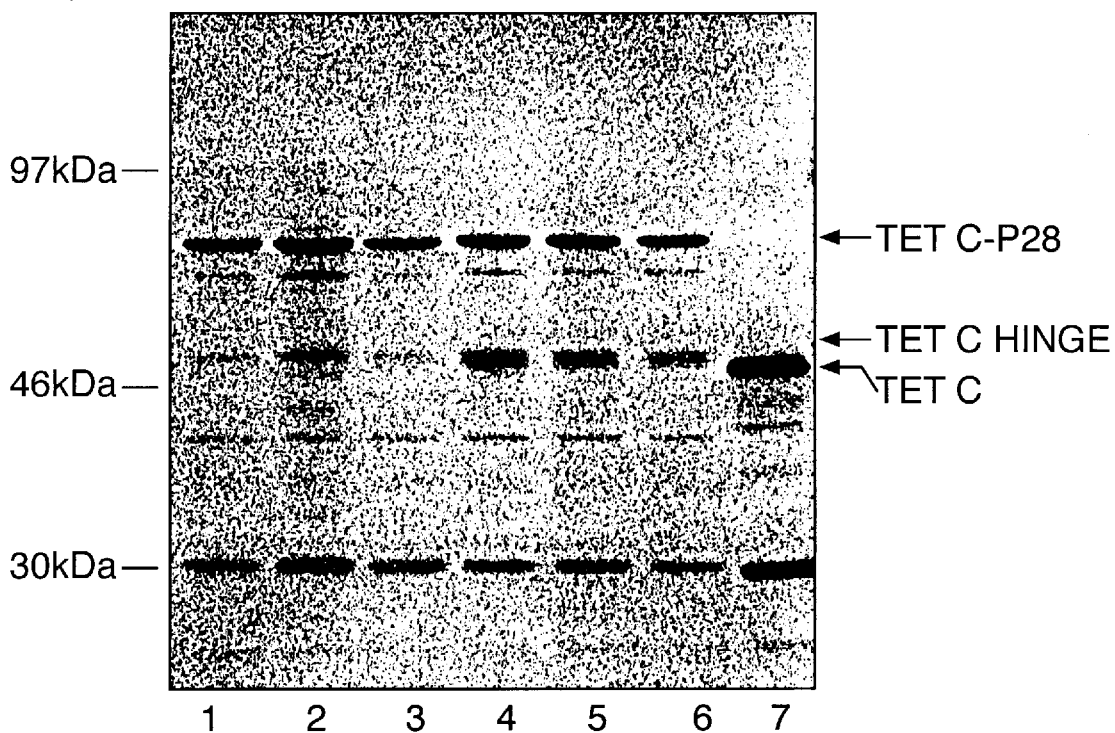
FIGS. 4 and 5 are western blots obtained from bacterial cells harbouring the pTECH3-P28 construct.
Figure 5:
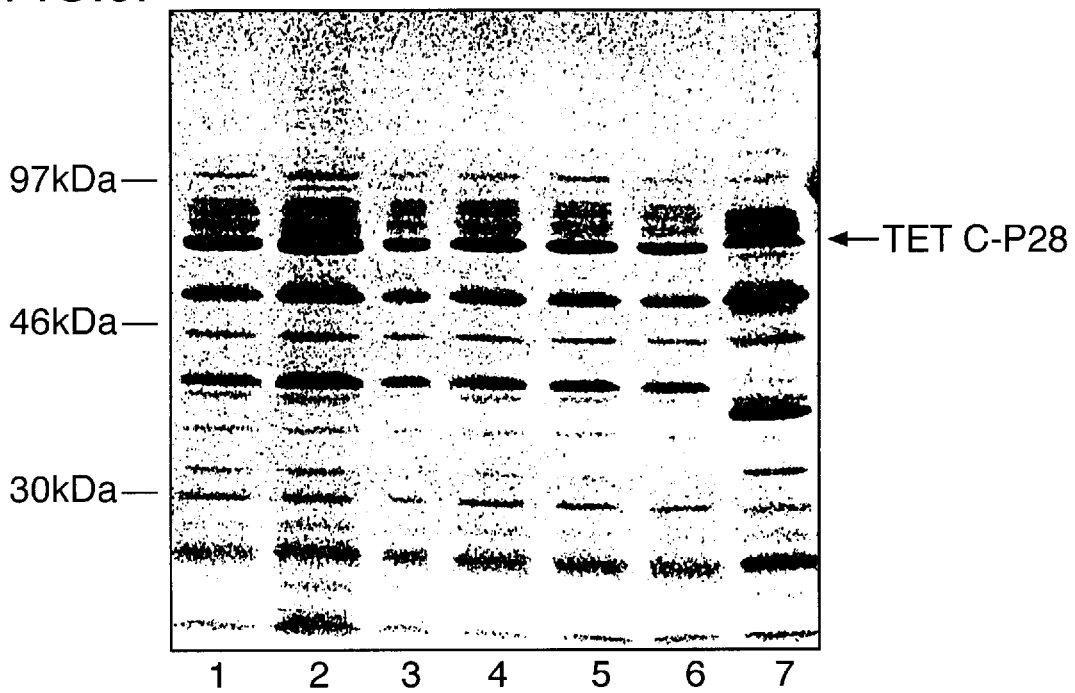

The preparation of pTECH1, a plasmid incorporating the nirB promoter and TetC gene, and a DNA sequence encoding a hinge region and containing restriction endonuclease sites to allow insertion of a gene coding for a second or guest protein, is illustrated in FIG. 1. Expression plasmid pTETnir15, the starting material shown in FIG. 1, was constructed from pTETtac115 (Makoff et al, Nucl. Acids Res. 17 10191–10202, 1989); by replacing the EcoRI-ApaI region (1354bp) containing the lacI gene and tac promoter with the following pair of oligos 1 and 2:

Oligo-1 5'AATTCAGGTAAATTTGATGTACAT-CAAATGGTACCCCTTGCTGAAT CGTTAAGGTAGGCGGTAGGGCC-3' (SEQ ID NO: 2)

Oligo-2 3'-GTCCATTTAAACTACATGTAGTTTACCATG GGGAACGACTTA GCAATTCCATCCGCCATC-5' (SEQ ID NO: 3)

The oligonucleotides were synthesised on a Pharmacia Gene Assembler and the resulting plasmids confirmed by sequencing (Makoff et al, Bio/Technology 7, 1043–1046, 1989).

The pTETnir15 plasmid was then used for construction of the pTECH1 plasmid incorporating a polylinker region suitable as a site for insertion of heterologous DNA to direct the expression of fragment C fusion proteins. pTETnir15 is a known pAT153-based plasmid which directs the expression of fragment C. However, there are no naturally occurring convenient restriction sites present at the 3'-end of the TetC gene. Therefore, target sites, preceded by a hinge region, were introduced at the 3'-end of the TetC coding region by means of primers SEQ ID NO: 4 and SEQ ID NO: 5 tailored with "add-on" adapter sequences (Table 1), using the polymerase chain reaction (PCR) [K. Mullis et al, Cold Spring Harbor Sym. Quant. Biol. 51, 263–273 1986]. Accordingly, pTETnir15 was used as a template in a PCR reaction using primers corresponding to regions covering the SacII and BamHI sites. The anti-sense primer in this amplification was tailored with a 38 base 5'-adaptor sequence. The anti-sense primer was designed so that a sequence encoding novel XbaI, SpeI and BamHI sites were incorporated into the PCR product. In addition, DNA sequences encoding additional extra amino acids including proline were incorporated (the hinge regions) and a translation stop codon signal in frame with the fragment C open reading frame.

The PCR product was gel-purified and digested with SacII and BamHI, and cloned into the residual 2.8 kb vector pTETnir15 which had previously been digested by SacII and BamHI. The resulting plasmid purified from transformed colonies and named pTECH 1 is shown in FIG. 1. Heterologous sequences such as the sequence encoding the *Schistosoma mansoni* P28 glutathione S-transferase (P28) were cloned into the XbaI SpeI and BamHI sites in accordance with known methods.

The DNA sequence of the plasmid pTECH1 is shown in the sequence listing as SEQ ID NO: 6.

TABLE 1

DNA SEQUENCES OF OLIGONUCLEOTIDES UTILISED IN THE CONSTRUCTION OF THE TETC-HINGE VECTORS

A). Primer 1.

Sense PCR (21mer). (SEQ ID NO: 4)
    SacII
 5'AAA GAC TCC GCG GGC GAA GTT-3'
    TETANUS TOXIN C FRAGMENT SEQ.

B). Primer 2.

Anti-Sense PCR Primer (64mer). (SEQ ID NO: 5)
   BamHI STOP SpeI   XbaI
5'-CTAT GGA TCC <u>TTA</u> ACT AGT GAT TCT AGA
 HINGE REGION
 GGG CCC CCG CCC GTC GTT GGT CCA ACC
 TTC ATC GGT -3'
  TETANUS TOXIN C FRAGMENT SEQ. 3'-END

EXAMPLE 2

Construction of pTECH1-P28

A P28 gene expression cassette was produced by PCR using pUC19-P28 DNA (a kind gift from Dr R Pierce, Pasteur Institute, Lille) as template. Oligonucleotide primers were designed to amplify the full length P28 gene beginning with the start codon and terminating with the stop codon. In addition, the sense and antisense primers were tailored with the restriction sites for XbaI and BamHI respectively. The primers are shown in the sequence listing as SEQ ID NO: 7 and SEQ ID NO: 8.

The product was gel-purified and digested with XbaI and BamHI and then cloned into pTECH1 which had previously been digested with these enzymes and subsequently gel-purified. The DNA sequence of pTECH1-P28 is shown in sequence listing as SEQ ID NO: 9.

Expression of the TetC-Hinge-P28 Fusion Protein

Several bacterial strains, namely *S. typhimirium* strains SL 5338 (A. Brown et al, J.Infect.Dis. 155, 86–92, 1987) and SL3261 and *E. coli* (TG2) were transformed with pTECH1-P28 by means of electroporation. SL3261 strains harbouring the pTECH1-P28 plasmid have been deposited at the National Collection of Type Cultures, 61 Colindale Avenue, London, NW9 5HT, UK under the accession number NCTC 12833. A strain of SL3261 containing the pTECH1 plasmid has been deposited under accession number NCTC 12831. The identity of recombinants was verified by restriction mapping of the plasmid DNA harboured by the cells. Further expression of the TetC-P28 fusion protein was then evaluated by SDS-PAGE and western blotting of bacterial cells harbouring the construct It was found that the fusion protein remains soluble, cross-reacts with antisera to both TetC and P28, and is also of the expected molecular weight, 80kDal, for a full length fusion.

The fusion protein was stably expressed in *E.coli* (TG2) and *S.* typhimurium (SL5338, SL3261) as judged by SDS-PAGE and western blotting. Of interest was a band of 50kDal which co-migrates with the TetC-Hinge protein alone and cross-reacts exclusively with the anti-TetC sera is visible in a western blot. As the codon selection in the hinge region has been designed to be suboptimal, the rare codons may cause pauses during translation which may occasionally lead to the premature termination of translation, thus accounting for this band.

Affinity Purification of the TetC-P28 Fusion

Glutathione is the natural substrate for P28, a glutathione S-transferase. The amino acid residues involved in binding glutathione are thought to be spatially separated in the primary structure of the polypeptide and brought together to form a glutathione binding pocket in the tertiary structure (P. Reinemer et al. EMBO, J8, 1997–2005, 1991). In order to gauge whether the P28 component of the fusion has folded correctly to adopt a conformation capable of binding glutathione, its ability to be affinity purified on a glutathione-agarose matrix was tested. The results obtained (not shown) demonstrated that TetC-P28 can indeed bind to the matrix and the binding is reversible, as the fusion can be competitively eluted with free glutathione.

EXAMPLE 3

Construction of TECH3-P28

The plasmid pTECH1-P28 directs the expression of the *S. mansoni* P28 protein as a C-terminal fusion to fragment C from tetanus toxin separated by a heterologous hinge domain. Expression of the fusion protein is under the control of the nirB promoter. The vector pTECH3-P28 was in part constructed from the plasmid pTETnir15 by the polymerase chain reaction (PCR) using the high fidelity thermostable DNA polymerase from *Pyrococcus fusorius*, which possesses an associated 3'5' exonuclease proofreading activity. The sequence of steps is summarised in FIG. 5. In order to generate a TetC-hingeless replacement cassette, the segment of DNA from the unique SacII site within the TetC gene to the final codon was amplified by means of the PCR reaction, using pTETnir15 as template DNA. The primers used in the PCR amplification are shown in the sequence listing as SEQ ID NO: 10 and SEQ ID NO: 11. The antisense primer in this amplification reaction was tailored with an XbaI recognition sequence.

The amplification reaction was performed according to the manufacturer's instructions (Stratagene, La Jolla, Calif., USA). The product was gel-purified, digested with SacII and XbaI, and then cloned into the residual pTECH1-P28 vector which had been previously digested with the respective enzymes SacII and XbaI. The resulting vector was designated pTECH3-P28. The DNA sequence of pTECH3-P28 is shown in the sequenc listing as SEQ ID NO: 12.

EXAMPLE 4

Transformation of *S. typhimurium* SL5338 (galE $r^-$ $m^+$) with pTECH3-P28, and Analysis of the Transformants

*S. typhimurium* SL5338 (galE $r^-m^+$) were cultured in either L or YT broth and on L-agar with ampicillin (50 g/ml) if appropriate and were transformed with the pTECH3-P28 plasmid. The transformation protocol was based on the method described by MacLachlan and Sanderson. (MacLachlan PR and Sanderson KE, 1985. Transformation of *Salmonella typhimurium* with plasmid DNA : differences between rough and smooth strains. J. Bacteriology 161, 442–445).

A 1ml overnight culture of *S. typhimurium* SL5338 ($r^-m^{30}$; Brown A, Hormaeche CE, Demarco de Hormaeche R, Dougan G, Winther M, Maskell D, and Stocker BAD, 1987. J. Infect.Dis. 155, 86–92) was used to inoculate 100 ml of LB broth and shaken at 37° C. until the culture reached $OD_{650}$=0.2. The cells were harvested at 3000×g and resuspended in 0.5 volumes if ice-cold 0.1M $MgCl_2$. The cells were pelleted again and resuspended in 0.5 volumes of ice-cold $CaCl_2$. This step was repeated once more and the cells resuspended in 1 ml of 0.1M $CaCl_2$ to which was added 50 $\mu$l of TES (50 mM Tris, 10 mM EDTA, 50 mM NaCl, pH 8.0). The cells were incubated on ice for 45 to 90 minutes. To 150$\mu$l of cells was added 100ng of plasmid DNA in 1–2 $\mu$l. The mixture was incubated on ice for 30 minutes prior to heat-shock at 42° C. for 2 minutes, and immediate reincubation on ice for 1 minute. To the transformed mixture was added 2 ml of LB broth and incubated for 1.5 hours to allow expression of the ampicillin drug resistance gene, B-lactamase. Following incubation 20 $\mu$l and 200 $\mu$l of cells were spread on to LB agar plates containing 50 $\mu$g/ml of ampicillin. The plates were dried and incubated at 37° C. overnight.

The identity of recombinants was verified by restriction mapping of the plasmid DNA and by western blotting with antisera directed against TetC and P28.

SDS-PAGE and Western Blotting

Expression of the TetC fusions was tested by SDS-PAGE and western blotting. *S. typhimurium* SL5338 (galE $r^-m^+$) bacterial cells containing the pTECH3-P28 plasmid and growing in mid-log phase, with antibiotic selection, were harvested by centrifugation and the proteins fractionated by 10% SDS-PAGE. The proteins were transferred to a nitrocellulose membrane by electroblotting and reacted with either a polyclonal rabbit antiserum directed against TetC or the full length P28 protein. The blots were then probed with goat anti-rabbit Ig conjugated to horse-radish peroxidase (Dako, High Wycombe, Bucks, UK) and developed with 4-chloro-1-napthol). The results of the western blotting experiments are shown in FIGS. 4 and 5; FIG. 4 illustrating the results of probing with rabbit anti-TetC polyclonal antiserum and FIG. 5 illustrates the results of probing with rabbit anti-P28 polyclonal antiserum. In each case lanes 1, 2 and 3 are independent clones of SL5338 (pTECH3-P28), lanes 4, 5 and 6 are SL5338 (pTECH1-P28) and lane 7 is SL5338 (pTETnir15). The molecular weight markers are indicated. From the results, it is evident that the fusion protein remains soluble, reacts with antisera to both TetC and P28, and is also of the expected molecular weight, 80 kDal, for a full length fusion (FIG. 4). Furthermore the fusion protein appears to be stably expressed.

Glutathione-Agarose Affinity Purification

Figure 6:
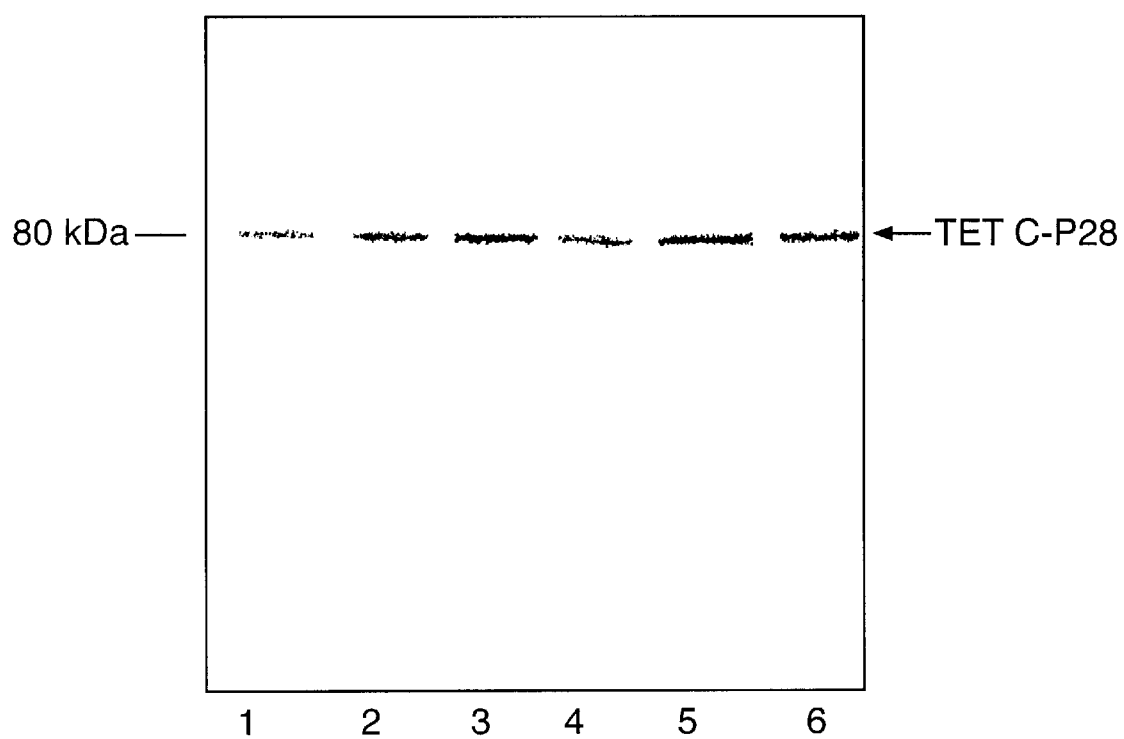
FIG. 6 illustrates the glutathione affinity purification of TetC fusions as determined by SDS-PAGE and Coomassie Blue Staining.

Glutathione is the natural substrate for P28, a glutathione S-transferase. The amino acid residues involved in binding glutathione are thought to be spatially separated in the primary structure of the polypeptide and brought together to form a glutathione binding pocket in the tertiary structure. In order to gauge whether the P28 component of the fusion has folded correctly to adopt a conformation capable of binding glutathione, we tested its ability to be affinity purified on a glutathione agarose matrix. Bacterial cells containing pTECH3-P28 and expressing the TetC full length P28 gene fusion were grown to log phase, chilled on ice, and harvested by centrifugation at 2500×g for 15 min at 4C. The cells were resuspended in ⅟₁₅th the original volume of ice-cold phosphate buffered saline (PBS) and lysed by sonication in a MSE Soniprep 150 (Gallenkamp, Leicester, UK). The insoluble material was removed by centrifugation and to the supernatant was added ⅙ volume of a 50% slurry of pre-swollen glutathione-agarose beads (Sigma, Poole, Dorset, UK). After mixing gently at room temperature for 1 hour the beads were collected by centrifugation at 1000×g for 10 secs. The supernatant was discarded and the beads resuspended in 20 volumes of cold PBS-0.5% Triton X100 and the beads collected again by centrifugation. The washing step was repeated three more times. The fusion protein was eluted by adding 1 volume of SDS-PAGE sample buffer. For comparison purposes, a similar procedure was followed with bacterial cells containing the PTECH1-P28 plasmid from which TetC-hinge-P28 fusion protein is expressed. Extracts from clones containing either plasmid were compared using SDS-PAGE and the results are shown in FIG. 6. In FIG. 6, lanes 1, 2 and 3 are clones of SL5338 (pTECH1-P28) whereas lanes 4, 5 and 6 are independent clones of SL 5338 (pTECH3-P28).

The results suggest that the TetC-P28 fusion protein can indeed bind to the matrix and the binding is reversible regardless of the absence of a heterologous hinge domain (data not shown) It is possible that a peptide sequence present at the C-terminus of TetC may in fact impart flexibility to this particular region.

```
                        SEQUENCE LISTING

<160> NUMBER OF SEQ ID NOS: 12

<210> SEQ ID NO 1
<211> LENGTH: 68
<212> TYPE: DNA
<213> ORGANISM: Escherichia coli

<400> SEQUENCE: 1
aattcaggta aatttgatgt acatcaaatg gtacccttg ctgaatcgtt aaggtaggcg      60
gtagggcc                                                             68

<210> SEQ ID NO 2
<211> LENGTH: 68
<212> TYPE: DNA
<213> ORGANISM: Artificial Sequence
<220> FEATURE:
<221> NAME/KEY: misc_feature
<222> LOCATION: (1)..(68)
<223> OTHER INFORMATION: Oligo-1 sequence

<400> SEQUENCE: 2
aattcaggta aatttgatgt acatcaaatg gtacccttg ctgaatcgtt aaggtaggcg      60
gtagggcc                                                             68

<210> SEQ ID NO 3
<211> LENGTH: 60
<212> TYPE: DNA
<213> ORGANISM: Artificial Sequence
<220> FEATURE:
<221> NAME/KEY: misc_feature
<222> LOCATION: (1)..(60)
<223> OTHER INFORMATION: Oligo-2 sequence

<400> SEQUENCE: 3
gtccatttaa actacatgta gtttaccatg gggaacgact tagcaattcc atccgccatc     60

<210> SEQ ID NO 4
<211> LENGTH: 21
<212> TYPE: DNA
<213> ORGANISM: Clostridium tetani

<400> SEQUENCE: 4
```

-continued

```
aaagactccg cgggcgaagt t                                              21

<210> SEQ ID NO 5
<211> LENGTH: 64
<212> TYPE: DNA
<213> ORGANISM: Clostridium tetani

<400> SEQUENCE: 5
ctatggatcc ttaactagtg attctagagg gccccggccc gtcgttggtc caaccttcat    60
cggt                                                                 64

<210> SEQ ID NO 6
<211> LENGTH: 3754
<212> TYPE: DNA
<213> ORGANISM: Artificial Sequence
<220> FEATURE:
<221> NAME/KEY: misc_feature
<222> LOCATION: (1)..(3754)
<223> OTHER INFORMATION: plasmid pTECH1

<400> SEQUENCE: 6
ttcaggtaaa tttgatgtac atcaaatggt accccttgct gaatcgttaa ggtaggcggt    60
agggcccaga tcttaatcat ccacaggaga ctttctgatg aaaaaccttg attgttgggt   120
cgacaacgaa gaagacatcg atgttatcct gaaaaagtct accattctga acttggacat   180
caacaacgat attatctccg acatctctgg tttcaactcc tctgttatca catatccaga   240
tgctcaattg gtgccgggca tcaacggcaa agctatccac ctggttaaca cgaatcttc    300 tgaagttatc gtgcacaagg ccatggacat cgaatacaac gacatgttca acaacttcac   360
cgttagcttc tggctgcgcg ttccgaaagt ttctgcttcc cacctggaac agtacggcac   420
taacgagtac tccatcatca gctctatgaa gaaacactcc ctgtccatcg gctctggttg   480
gtctgtttcc ctgaagggta caacctgat ctggactctg aaagactccg cgggcgaagt   540
tcgtcagatc actttccgcg acctgccgga caagttcaac gcgtacctgg ctaacaaatg   600
ggttttcatc actatcacta cgatcgtct gtcttctgct aacctgtaca tcaacggcgt   660
tctgatgggc tccgctgaaa tcactggtct gggcgctatc cgtgaggaca caacatcac   720 tcttaagctg gaccgttgca caacaacaa ccagtacgta tccatcgaca gttccgtat   780 cttctgcaaa gcactgaacc cgaaagagat cgaaaaactg tataccagct acctgtctat   840
caccttcctg cgtgacttct ggggtaaccc gctgcgttac gacaccgaat attacctgat   900
cccggtagct tctagctcta agacgttca gctgaaaaac atcactgact acatgtacct   960
gaccaacgcg ccgtcctaca ctaacggtaa actgaacatc tactaccgac gtctgtacaa  1020
cggcctgaaa ttcatcatca aacgctacac tccgaacaac gaaatcgatt ctttcgttaa  1080
atctggtgac ttcatcaaac tgtacgtttc ttacaacaac aacgaacaca tcgttggtta  1140
cccgaaagac ggtaacgctt tcaacaacct ggacagaatt ctgcgtgttg gttacaacgc  1200
tccgggtatc ccgctgtaca aaaaatgga agctgttaaa ctgcgtgacc tgaaaaccta  1260
ctctgttcag ctgaaactgt acgacgacaa aaacgcttct ctgggtctgg ttggtaccca  1320
caacggtcag atcggtaacg acccgaaccg tgacatcctg atcgcttcta ctggtactt  1380 caaccacctg aaagacaaaa tcctgggttg cgactggtac ttcgttccga ccgatgaagg  1440
ttggaccaac gacgggccgg ggccctctag aatcactagt taaggatccg ctagcccgcc  1500
taatgagcgg gcttttttt ctcgggcagc gttgggtcct ggccacgggt gcgcatgatc  1560
```

-continued

```
gtgctcctgt cgttgaggac ccggctaggc tggcggggtt gccttactgg ttagcagaat   1620
gaatcaccga tacgcgagcg aacgtgaagc gactgctgct gcaaaacgtc tgcgacctga   1680
gcaacaacat gaatggtctt cggtttccgt gtttcgtaaa gtctggaaac gcggaagtca   1740
gcgctcttcc gcttcctcgc tcactgactc gctgcgctcg tcgttcggc tgcggcgagc   1800 ggtatcagct cactcaaagg cggtaatacg gttatccaca gaatcagggg ataacgcagg   1860
aaagaacatg tgagcaaaag gccagcaaaa ggccaggaac cgtaaaaagg ccgcgttgct   1920
ggcgtttttc cataggctcc gcccccctga cgagcatcac aaaaatcgac gctcaagtca   1980
gaggtggcga acccgacag gactataaag ataccaggcg tttccccctg gaagctccct   2040
cgtgcgctct cctgttccga ccctgccgct taccggatac ctgtccgcct ttctcccttc   2100
gggaagcgtg gcgctttctc aatgctcacg ctgtaggtat ctcagttcgg tgtaggtcgt   2160
tcgctccaag ctgggctgtg tgcacgaacc ccccgttcag cccgaccgct gcgccttatc   2220
cggtaactat cgtcttgagt ccaacccggt aagacacgac ttatcgccac tggcagcagc   2280
cactggtaac aggattagca gagcgaggta tgtaggcggt gctacagagt tcttgaagtg   2340
gtggcctaac tacggctaca ctagaaggac agtatttggt atctgcgctc tgctgaagcc   2400
agttaccttc ggaaaaagag ttggtagctc ttgatccggc aaacaaacca ccgctggtag   2460
cggtggtttt tttgtttgca agcagcagat tacgcgcaga aaaaaggat ctcaagaaga   2520 tcctttgatc ttttctacgg ggtctgacgc tcagtggaac gaaaactcac gttaagggat   2580
tttggtcatg agattatcaa aaaggatctt cacctagatc cttttaaatt aaaaatgaag   2640
ttttaaatca atctaaagta tatatgagta aacttggtct gacagttacc aatgcttaat   2700
cagtgaggca cctatctcag cgatctgtct atttcgttca tccatagttg cctgactccc   2760
cgtcgtgtag ataactacga tacgggaggg cttaccatct ggccccagtg ctgcaatgat   2820
accgcgagac ccacgctcac cggctccaga tttatcagca ataaaccagc cagccggaag   2880
ggccgagcgc agaagtggtc ctgcaacttt atccgcctcc atccagtcta ttaattgttg   2940
ccgggaagct agagtaagta gttcgccagt taatagtttg cgcaacgttg ttgccattgc   3000
tgcaggcatc gtggtgtcac gctcgtcgtt tggtatggct tcattcagct ccggttccca   3060
acgatcaagg cgagttacat gatcccccat gttgtgcaaa aaagcggtta gctccttcgg   3120
tcctccgatc gttgtcagaa gtaagttggc cgcagtgtta tcactcatgg ttatggcagc   3180
actgcataat tctcttactg tcatgccatc cgtaagatgc ttttctgtga ctggtgagta   3240
ctcaaccaag tcattctgag aatagtgtat gcggcgaccg agttgctctt gcccggcgtc   3300
aacacgggat aataccgcgc cacatagcag aactttaaaa gtgctcatca ttggaaaacg   3360
ttcttcgggg cgaaaactct caaggatctt accgctgttg agatccagtt cgatgtaacc   3420
cactcgtgca cccaactgat cttcagcatc ttttactttc accagcgttt ctgggtgagc   3480
aaaaacagga aggcaaaatg ccgcaaaaaa gggaataagg gcgacacgga aatgttgaat   3540
actcatactc ttccttttc aatattattg aagcatttat cagggttatt gtctcatgag   3600
cggatacata tttgaatgta tttagaaaaa taaacaaata ggggttccgc gcacatttcc   3660
ccgaaaagtg ccacctgacg tctaagaaac cattattatc atgacattaa cctataaaaa   3720
taggcgtatc acgaggccct ttcgtcttca agaa                                3754
```

<210> SEQ ID NO 7
<211> LENGTH: 30
<212> TYPE: DNA
<213> ORGANISM: Schistosoma mansoni -continued

<400> SEQUENCE: 7
tagtctagaa tggctggcga gcatatcaag         30

<210> SEQ ID NO 8
<211> LENGTH: 30
<212> TYPE: DNA
<213> ORGANISM: Schistosoma mansoni

<400> SEQUENCE: 8
ttaggatcct tagaagggag ttgcaggcct         30

<210> SEQ ID NO 9
<211> LENGTH: 4378
<212> TYPE: DNA
<213> ORGANISM: Artificial Sequence
<220> FEATURE:
<221> NAME/KEY: misc_feature
<222> LOCATION: (1)..(4378)
<223> OTHER INFORMATION: plasmid pTECH1-P28
<221> NAME/KEY: misc_feature
<222> LOCATION: (98)..(100)
<223> OTHER INFORMATION: Tet C gene start codon
<221> NAME/KEY: misc_feature
<222> LOCATION: (528)..(533)
<223> OTHER INFORMATION: SacII restriction site
<221> NAME/KEY: misc_feature
<222> LOCATION: (1454)..(1465)
<223> OTHER INFORMATION: hinge domain
<221> NAME/KEY: misc_feature
<222> LOCATION: (1466)..(1471)
<223> OTHER INFORMATION: XbaI restriction site
<221> NAME/KEY: misc_feature
<222> LOCATION: (1472)..(1474)
<223> OTHER INFORMATION: S. mansoni P28 gene start codon
<221> NAME/KEY: misc_feature
<222> LOCATION: (2105)..(2107)
<223> OTHER INFORMATION: stop codon
<221> NAME/KEY: misc_feature
<222> LOCATION: (2108)..(2113)
<223> OTHER INFORMATION: BamHI restriction site

<400> SEQUENCE: 9
ttcaggtaaa tttgatgtac atcaaatggt acccctgct gaatcgttaa ggtaggcggt    60
agggcccaga tcttaatcat ccacaggaga ctttctgatg aaaaaccttg attgttgggt   120
cgacaacgaa gaagacatcg atgttatcct gaaaaagtct accattctga acttggacat   180
caacaacgat attatctccg acatctctgg tttcaactcc tctgttatca catatccaga   240
tgctcaattg gtgccgggca tcaacggcaa agctatccac ctggttaaca cgaatcttc    300 tgaagttatc gtgcacaagg ccatggacat cgaatacaac gacatgttca acaacttcac   360
cgttagcttc tggctgcgcg ttccgaaagt ttctgcttcc cacctggaac agtacggcac   420
taacgagtac tccatcatca gctctatgaa gaaacactcc ctgtccatcg gctctggttg   480
gtctgtttcc ctgaagggta caacctgat ctggactctg aaagactccg cgggcgaagt   540
tcgtcagatc actttccgcg acctgccgga caagttcaac gcgtacctgg ctaacaaatg   600
ggttttcatc actatcacta cgatcgtct gtcttctgct aacctgtaca tcaacggcgt   660
tctgatgggc tccgctgaaa tcactggtct gggcgctatc cgtgaggaca caacatcac   720 tcttaagctg gaccgttgca caacaacaa ccagtacgta tccatcgaca gttccgtat    780 cttctgcaaa gcactgaacc cgaaagagat cgaaaaactg tataccagct acctgtctat   840
caccttcctg cgtgacttct ggggtaaccc gctgcgttac gacaccgaat attacctgat   900
cccggtagct tctagctcta aagacgttca gctgaaaaac atcactgact acatgtacct   960

```
gaccaacgcg ccgtcctaca ctaacggtaa actgaacatc tactaccgac gtctgtacaa   1020
cggcctgaaa ttcatcatca aacgctacac tccgaacaac gaaatcgatt ctttcgttaa   1080
atctggtgac ttcatcaaac tgtacgtttc ttacaacaac aacgaacaca tcgttggtta   1140
cccgaaagac ggtaacgctt tcaacaacct ggacagaatt ctgcgtgttg gttacaacgc   1200
tccgggtatc ccgctgtaca aaaaatgga agctgttaaa ctgcgtgacc tgaaaaccta   1260
ctctgttcag ctgaaactgt acgacgacaa aaacgcttct ctgggtctgg ttggtaccca   1320
caacggtcag atcggtaacg acccgaaccg tgacatcctg atcgcttcta actggtactt   1380
caaccacctg aaagacaaaa tcctgggttg cgactggtac ttcgttccga ccgatgaagg   1440
ttggaccaac gacgggccgg ggccctctag aatggctggc gagcatatca aggttatcta   1500
ttttgacgga cgcggacgtg ctgaatcgat tcggatgact cttgtggcag ctggtgtaga   1560
ctacgaagat gagagaatta gtttccaaga ttggccaaaa atcaaaccaa ctattccaga   1620
cggacgattg cctgcagtga aagtcactga tgatcatggg cacgtgaaat ggatgttaga   1680
gagtttggct attgcacggt atatggcgaa gaaacatcat atgatgggtg aaacagacga   1740
ggaatactat agtgttgaaa agttgattgg tcatgctgaa gatgtagaac atgaatatca   1800
caaaactttg atgaagccac aagaagagaa agagaagata accaaagaga tattgaacgg   1860
caaagttcca gttcttctca atatgatctg cgaatctctg aaagggtcga caggaaagct   1920
ggctgttggg gacaaagtaa ctctagctga tttagtcctg attgctgtca ttgatcatgt   1980
gactgatctg gataaaggat ttctaactgg caagtatcct gagatccata acatcgaga   2040 aaatctgtta gccagttcac cgcgtttggc gaaatattta tcgaacaggc ctgcaactcc   2100
cttctaagga tccgctagcc cgcctaatga gcgggctttt ttttctcggg cagcgttggg   2160
tcctggccac gggtgcgcat gatcgtgctc ctgtcgttga ggacccggct aggctggcgg   2220
ggttgcctta ctggttagca gaatgaatca ccgatacgcg agcgaacgtg aagcgactgc   2280
tgctgcaaaa cgtctgcgac ctgagcaaca acatgaatgg tcttcggttt ccgtgtttcg   2340
taaagtctgg aaacgcggaa gtcagcgctc ttccgcttcc tcgctcactg actcgctgcg   2400
ctcggtcgtt cggctgcggc gagcggtatc agctcactca aaggcggtaa tacggttatc   2460
cacagaatca ggggataacg caggaaagaa catgtgagca aaaggccagc aaaaggccag   2520
gaaccgtaaa aaggccgcgt tgctggcgtt tttccatagg ctccgccccc ctgacgagca   2580
tcacaaaaat cgacgctcaa gtcagaggtg gcgaaacccg acaggactat aaagatacca   2640
ggcgtttccc cctggaagct ccctcgtgcg ctctcctgtt ccgaccctgc cgcttaccgg   2700
atacctgtcc gcctttctcc cttcgggaag cgtggcgctt tctcaatgct cacgctgtag   2760
gtatctcagt tcggtgtagg tcgttcgctc caagctgggc tgtgtgcacg aaccccccgt   2820
tcagcccgac cgctgcgcct tatccggtaa ctatcgtctt gagtccaacc cggtaagaca   2880
cgacttatcg ccactggcag cagccactgg taacaggatt agcagagcga ggtatgtagg   2940
cggtgctaca gagttcttga agtggtggcc taactacggc tacactagaa ggacagtatt   3000
tggtatctgc gctctgctga agccagttac cttcggaaaa agagttggta gctcttgatc   3060
cggcaaacaa accaccgctg gtagcggtgg tttttttgtt tgcaagcagc agattacgcg   3120
cagaaaaaaa ggatctcaag aagatccttt gatcttttct acgggtctga cgctcagtg   3180 gaacgaaaac tcacgttaag ggattttggt catgagatta tcaaaaagga tcttcaccta   3240
gatcctttta aattaaaaat gaagttttaa atcaatctaa agtatatatg agtaaacttg   3300
```

```
gtctgacagt taccaatgct taatcagtga ggcacctatc tcagcgatct gtctatttcg    3360
ttcatccata gttgcctgac tccccgtcgt gtagataact acgatacggg agggcttacc    3420
atctggcccc agtgctgcaa tgataccgcg agacccacgc tcaccggctc cagatttatc    3480
agcaataaac cagccagccg gaagggccga gcgcagaagt ggtcctgcaa ctttatccgc    3540
ctccatccag tctattaatt gttgccggga agctagagta agtagttcgc cagttaatag    3600
tttgcgcaac gttgttgcca ttgctgcagg catcgtggtg tcacgctcgt cgtttggtat    3660
ggcttcattc agctccggtt cccaacgatc aaggcgagtt acatgatccc ccatgttgtg    3720
caaaaaagcg gttagctcct tcggtcctcc gatcgttgtc agaagtaagt tggccgcagt    3780
gttatcactc atggttatgg cagcactgca taattctctt actgtcatgc catccgtaag    3840
atgcttttct gtgactggtg agtactcaac caagtcattc tgagaatagt gtatgcggcg    3900
accgagttgc tcttgcccgg cgtcaacacg ggataatacc gcgccacata gcagaacttt    3960
aaaagtgctc atcattggaa acgttcttc ggggcgaaaa ctctcaagga tcttaccgct    4020
gttgagatcc agttcgatgt aacccactcg tgcacccaac tgatcttcag catcttttac    4080
tttcaccagc gtttctgggt gagcaaaaac aggaaggcaa aatgccgcaa aaaagggaat    4140
aagggcgaca cggaaatgtt gaatactcat actcttcctt tttcaatatt attgaagcat    4200
ttatcagggt tattgtctca tgagcggata catatttgaa tgtatttaga aaataaaca    4260 aatagggggtt ccgcgcacat ttccccgaaa agtgccacct gacgtctaag aaaccattat    4320
tatcatgaca ttaacctata aaataggcg tatcacgagg ccctttcgtc ttcaagaa      4378
```

<210> SEQ ID NO 10
<211> LENGTH: 21
<212> TYPE: DNA
<213> ORGANISM: Clostridium tetani

<400> SEQUENCE: 10

```
aaagactccg cgggcgaagt t                                               21
```

<210> SEQ ID NO 11
<211> LENGTH: 30
<212> TYPE: DNA
<213> ORGANISM: Clostridium tetani

<400> SEQUENCE: 11

```
ttatctagag tcgttggtcc aaccttcatc                                      30
```

<210> SEQ ID NO 12
<211> LENGTH: 4366
<212> TYPE: DNA
<213> ORGANISM: Artificial Sequence
<220> FEATURE:
<221> NAME/KEY: misc_feature
<222> LOCATION: (1)..(4366)
<223> OTHER INFORMATION: plasmid pTECH3-P28
<221> NAME/KEY: misc_feature
<222> LOCATION: (98)..(100)
<223> OTHER INFORMATION: Tet C gene start codon
<221> NAME/KEY: misc_feature
<222> LOCATION: (528)..(533)
<223> OTHER INFORMATION: SacII restriction site
<221> NAME/KEY: misc_feature
<222> LOCATION: (1454)..(1459)
<223> OTHER INFORMATION: XbaI restriction site
<221> NAME/KEY: misc_feature
<222> LOCATION: (1460)..(1462)
<223> OTHER INFORMATION: S. mansoni P28 gene start codon
<221> NAME/KEY: misc_feature
<222> LOCATION: (2093)..(2095)

<223> OTHER INFORMATION: stop codon
<221> NAME/KEY: misc_feature
<222> LOCATION: (2096)..(2101)
<223> OTHER INFORMATION: BamHI restriction site

<400> SEQUENCE: 12

| | | | | | |
|---|---|---|---|---|---|
| ttcaggtaaa | tttgatgtac | atcaaatggt | accccttgct | gaatcgttaa | ggtaggcggt | 60 |
| agggcccaga | tcttaatcat | ccacaggaga | ctttctgatg | aaaaaccttg | attgttgggt | 120 |
| cgacaacgaa | gaagacatcg | atgttatcct | gaaaaagtct | accattctga | acttggacat | 180 |
| caacaacgat | attatctccg | acatctctgg | tttcaactcc | tctgttatca | catatccaga | 240 |
| tgctcaattg | gtgccgggca | tcaacggcaa | agctatccac | ctggttaaca | acgaatcttc | 300 |
| tgaagttatc | gtgcacaagg | ccatggacat | cgaatacaac | gacatgttca | acaacttcac | 360 |
| cgttagcttc | tggctgcgcg | ttccgaaagt | ttctgcttcc | cacctggaac | agtacggcac | 420 |
| taacgagtac | tccatcatca | gctctatgaa | gaaacactcc | ctgtccatcg | gctctggttg | 480 |
| gtctgtttcc | ctgaagggta | caacctgat | ctggactctg | aaagactccg | cgggcgaagt | 540 |
| tcgtcagatc | actttccgcg | acctgccgga | caagttcaac | gcgtacctgg | ctaacaaatg | 600 |
| ggttttcatc | actatcacta | cgatcgtct | gtcttctgct | aacctgtaca | tcaacggcgt | 660 |
| tctgatgggc | tccgctgaaa | tcactggtct | ggcgctatc | cgtgaggaca | caacatcac | 720 |
| tcttaagctg | gaccgttgca | caacaacaa | ccagtacgta | tccatcgaca | gttccgtat | 780 |
| cttctgcaaa | gcactgaacc | cgaaagagat | cgaaaaactg | tataccagct | acctgtctat | 840 |
| caccttcctg | cgtgacttct | ggggtaaccc | gctgcgttac | gacaccgaat | attacctgat | 900 |
| cccggtagct | tctagctcta | aagacgttca | gctgaaaaac | atcactgact | acatgtacct | 960 |
| gaccaacgcg | ccgtcctaca | ctaacggtaa | actgaacatc | tactaccgac | gtctgtacaa | 1020 |
| cggcctgaaa | ttcatcatca | aacgctacac | tccgaacaac | gaaatcgatt | ctttcgttaa | 1080 |
| atctggtgac | ttcatcaaac | tgtacgtttc | ttacaacaac | aacgaacaca | tcgttggtta | 1140 |
| cccgaaagac | ggtaacgctt | tcaacaacct | ggacagaatt | ctgcgtgttg | gttacaacgc | 1200 |
| tccgggtatc | ccgctgtaca | aaaaaatgga | agctgttaaa | ctgcgtgacc | tgaaaaccta | 1260 |
| ctctgttcag | ctgaaactgt | acgacgacaa | aaacgcttct | ctgggtctgg | ttggtaccca | 1320 |
| caacggtcag | atcggtaacg | acccgaaccg | tgacatcctg | atcgcttcta | actggtactt | 1380 |
| caaccacctg | aaagacaaaa | tcctgggttg | cgactggtac | ttcgttccga | ccgatgaagg | 1440 |
| ttggaccaac | gactctagaa | tggctggcga | gcatatcaag | gttatctatt | ttgacggacg | 1500 |
| cggacgtgct | gaatcgattc | ggatgactct | tgtggcagct | ggtgtagact | acgaagatga | 1560 |
| gagaattagt | ttccaagatt | ggccaaaaat | caaaccaact | attccagacg | gacgattgcc | 1620 |
| tgcagtgaaa | gtcactgatg | atcatgggca | cgtgaaatgg | atgttagaga | gtttggctat | 1680 |
| tgcacggtat | atggcgaaga | acatcatat | gatgggtgaa | acagacgagg | aatactatag | 1740 |
| tgttgaaaag | ttgattggtc | atgctgaaga | tgtagaacat | gaatatcaca | aactttgat | 1800 |
| gaagccacaa | gaagagaaag | agaagataac | caaagagata | ttgaacggca | aagttccagt | 1860 |
| tcttctcaat | atgatctgcg | aatctctgaa | agggtcgaca | ggaaagctgg | ctgttgggga | 1920 |
| caaagtaact | ctagctgatt | tagtcctgat | tgctgtcatt | gatcatgtga | ctgatctgga | 1980 |
| taaaggattt | ctaactggca | agtatcctga | gatccataaa | catcgagaaa | atctgttagc | 2040 |
| cagttcaccg | cgtttggcga | aatatttatc | gaacaggcct | gcaactccct | tctaaggatc | 2100 |
| cgctagcccg | cctaatgagc | gggcttttt | ttctcgggca | gcgttgggtc | ctggccacgg | 2160 |

-continued

```
gtgcgcatga tcgtgctcct gtcgttgagg acccggctag gctggcgggg ttgccttact   2220
ggttagcaga atgaatcacc gatacgcgag cgaacgtgaa gcgactgctg ctgcaaaacg   2280
tctgcgacct gagcaacaac atgaatggtc ttcggtttcc gtgtttcgta aagtctggaa   2340
acgcggaagt cagcgctctt ccgcttcctc gctcactgac tcgctgcgct cggtcgttcg   2400
gctgcggcga gcggtatcag ctcactcaaa ggcggtaata cggttatcca cagaatcagg   2460
ggataacgca ggaaagaaca tgtgagcaaa aggccagcaa aaggccagga accgtaaaaa   2520
ggccgcgttg ctggcgtttt tccataggct ccgcccccct gacgagcatc acaaaaatcg   2580
acgctcaagt cagaggtggc gaaacccgac aggactataa agataccagg cgtttccccc   2640
tggaagctcc ctcgtgcgct ctcctgttcc gaccctgccg cttaccggat acctgtccgc   2700
ctttctccct tcgggaagcg tggcgctttc tcaatgctca cgctgtaggt atctcagttc   2760
ggtgtaggtc gttcgctcca agctgggctg tgtgcacgaa ccccccgttc agcccgaccg   2820
ctgcgcctta tccggtaact atcgtcttga gtccaacccg gtaagacacg acttatcgcc   2880
actggcagca gccactggta acaggattag cagagcgagg tatgtaggcg gtgctacaga   2940
gttcttgaag tggtggccta actacggcta cactagaagg acagtatttg gtatctgcgc   3000
tctgctgaag ccagttacct tcggaaaaag agttggtagc tcttgatccg gcaaacaaac   3060
caccgctggt agcggtggtt ttttgtttg caagcagcag attacgcgca gaaaaaaagg   3120
atctcaagaa gatcctttga tcttttctac ggggtctgac gctcagtgga cgaaaactc    3180 acgttaaggg attttggtca tgagattatc aaaaaggatc ttcacctaga tccttttaaa   3240
ttaaaaatga agttttaaat caatctaaag tatatatgag taaacttggt ctgacagtta   3300
ccaatgctta atcagtgagg cacctatctc agcgatctgt ctatttcgtt catccatagt   3360
tgcctgactc cccgtcgtgt agataactac gatacgggag gcttaccat ctggccccag    3420 tgctgcaatg ataccgcgag acccacgctc accggctcca gatttatcag caataaacca   3480
gccagccgga agggccgagc gcagaagtgg tcctgcaact ttatccgcct ccatccagtc   3540
tattaattgt tgccgggaag ctagagtaag tagttcgcca gttaatagtt tgcgcaacgt   3600
tgttgccatt gctgcaggca tcgtggtgtc acgctcgtcg tttggtatgg cttcattcag   3660
ctccggttcc caacgatcaa ggcgagttac atgatccccc atgttgtgca aaaaagcggt   3720
tagctccttc ggtcctccga tcgttgtcag aagtaagttg gccgcagtgt tatcactcat   3780
ggttatggca gcactgcata attctcttac tgtcatgcca tccgtaagat gcttttctgt   3840
gactggtgag tactcaacca agtcattctg agaatagtgt atgcggcgac cgagttgctc   3900
ttgcccggcg tcaacacggg ataataccgc gccacatagc agaactttaa aagtgctcat   3960
cattggaaaa cgttcttcgg ggcgaaaact ctcaaggatc ttaccgctgt tgagatccag   4020
ttcgatgtaa cccactcgtg cacccaactg atcttcagca tcttttactt tcaccagcgt   4080
ttctgggtga gcaaaaacag gaaggcaaaa tgccgcaaaa aagggaataa gggcgacacg   4140
gaaatgttga atactcatac tcttcctttt tcaatattat tgaagcattt atcagggtta   4200
ttgtctcatg agcggataca tatttgaatg tatttagaaa aataaacaaa tagggttcc    4260 gcgcacattt ccccgaaaag tgccacctga cgtctaagaa accattatta tcatgacatt   4320
aacctataaa aataggcgta tcacgaggcc tttcgtctt caagaa                   4366
``` what is claimed is:

1. A DNA construct comprising a DNA sequence encoding a fusion protein of the formula TetC-$(Z)_a$-Het, wherein TetC is the C fragment of tetanus toxin, Het is a heterologous protein, Z is an amino acid, and a is 0 or a positive integer less than 4, provided that $(Z)_a$ does not include the sequence Gly-Pro, wherein the amino terminus of the fusion protein is the TetC.

2. A DNA construct according to claim 1 wherein $(Z)_a$ is a chain of two or three amino acids, the DNA sequence for which defines a restriction endonuclease cleavage site.

3. A DNA construct according to claim 1 wherein a is zero.

4. A DNA construct according to claim 1 in which $(Z)_a$ is free from glycine and/or proline.

5. A DNA construct according to claim 1 wherein the heterologous protein Het is an antigenic sequence obtained from a virus, bacterium, fungus, yeast or parasite.

6. A DNA construct according to claim 5 wherein the heterologous protein Het is the *Schistosoma mansoni* P28 glutathione S-transferase antigen.

7. A replicable expression vector containing a DNA construct as defined in claim 1.

8. A replicable expression vector according to claim 7 suitable for use in bacteria.

9. A host cell having integrated into the chromosomal DNA thereof a DNA construct as defined in claim 1.

10. A host cell according to claim 9 which is a bacterium.

11. A fusion protein of the formula TetC-$(Z)_a$-Het, wherein TetC is the C fragment of tetanus toxin, Het is a heterologous protein, Z is an amino acid, and a is 0 or a positive integer less than 4, provided that $(Z)_a$ does not include the sequence Gly-Pro, wherein the amino terminus of the fusion protein is the TetC.

12. A process for the preparation of a bacterium which process comprises transforming a bacterium with a DNA construct as defined in claim 1.

13. A process according to claim 12 wherein the bacterium is an attenuated bacterium.

14. A vaccine composition comprising a fusion protein as defined in claim 11 and a pharmaceutically acceptable carrier.

15. A vaccine composition comprising an attenuated bacterium expressing a fusion protein as defined in claim 2; and a pharmaceutically acceptable carrier.

16. A replicable expression vector containing a DNA construct as defined in claim 2.

17. A replicable expression vector according to claim 16 suitable for use in bacteria.

18. A host cell having integrated into the chromosomal DNA thereof a DNA construct as defined in claim 2.

19. A host cell according to claim 18 which is a bacterium.

20. A vaccine composition comprising an attenuated bacterium containing a DNA construct as defined in claim 2; and a pharmaceutically acceptable carrier.

21. A fusion protein of the formula TetC-$(Z)_a$-Het, wherein TetC is the C fragment of tetanus toxin, Het is a heterologous protein, $(Z)_a$ is a chain of two or three amino acids, the DNA sequence for which defines a restriction endonuclease cleavage site, wherein the amino terminus of the fusion protein is the TetC.

22. A vaccine composition containing a fusion protein as defined in claim 21 and a pharmaceutically acceptable carrier.

* * * * *